(12) United States Patent
Fitz et al.

(10) Patent No.: US 10,058,330 B2
(45) Date of Patent: Aug. 28, 2018

(54) DEVICE FOR OCCLUDING A LUMEN

(75) Inventors: Matthew Fitz, Vista, CA (US); Tai D. Tieu, Fountain Valley, CA (US); Shawn O'Leary, San Juan Capistrano, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 42 days.

(21) Appl. No.: 13/470,066

(22) Filed: May 11, 2012

(65) Prior Publication Data

US 2012/0316597 A1   Dec. 13, 2012

Related U.S. Application Data

(60) Provisional application No. 61/485,065, filed on May 11, 2011.

(51) Int. Cl.
*A61B 17/12* (2006.01)

(52) U.S. Cl.
CPC .... *A61B 17/12031* (2013.01); *A61B 17/1214* (2013.01); *A61B 17/1219* (2013.01);
(Continued)

(58) Field of Classification Search
CPC ...... A61B 17/0057; A61B 2017/00637; A61B 2017/00654; A61B 2017/00898; A61B 2017/00676; A61B 17/1219
See application file for complete search history.

(56) References Cited

U.S. PATENT DOCUMENTS

| 3,868,956 A | 3/1975 | Alfidi |
| 4,130,904 A | 12/1978 | Whalen |

(Continued)

FOREIGN PATENT DOCUMENTS

| EP | 0107055 A2 | 5/1984 |
| EP | 0441516 A2 | 8/1991 |

(Continued)

OTHER PUBLICATIONS

WIPO, International Preliminary Examining Authority (U.S. Patent and Trademark Office), International Preliminary Report on Patentability dated Nov. 21, 2013 in International Patent Application No. PCT/US2012/037621, 7 pages.

(Continued)

*Primary Examiner* — Katherine M Shi
*Assistant Examiner* — Michael Mendoza
(74) *Attorney, Agent, or Firm* — Inskeep IP Group, Inc.

(57) ABSTRACT

One embodiment according to the present invention includes an occlusion device in which the support structure or frame expands circumferentially within the lumen to secure an expansile plug or embolic material. Once in place, the expansile plug or embolic material expands, thereby occluding the target lumen. Another embodiment according to the present invention includes a radially expandable support structure having a closed portion for capturing subsequently delivered embolic material, such as embolic coils. For example, the structure may have a closed portion at its distal end or at its middle (forming an hourglass shape). Additionally, the closed portion may be formed from the support structure itself or from a discrete, second layer that is attached within the support structure.

3 Claims, 9 Drawing Sheets

(52) U.S. Cl.
CPC .. *A61B 17/12109* (2013.01); *A61B 17/12172* (2013.01); *A61B 17/12177* (2013.01); *A61B 17/12181* (2013.01)

(56) References Cited

U.S. PATENT DOCUMENTS

| | | | |
|---|---|---|---|
| 4,140,126 A | 2/1979 | Choudhury |
| 4,286,341 A | 9/1981 | Greer et al. |
| 4,512,338 A | 4/1985 | Balko et al. |
| 4,553,545 A | 11/1985 | Maass et al. |
| 4,562,596 A | 1/1986 | Kornberg |
| 4,577,631 A | 3/1986 | Kreamer |
| 4,655,771 A | 4/1987 | Wallsten |
| 4,663,358 A | 5/1987 | Hyon et al. |
| 4,733,665 A | 3/1988 | Palmaz |
| 4,734,097 A | 3/1988 | Tanabe et al. |
| 4,740,207 A | 4/1988 | Kreamer |
| 4,768,507 A | 9/1988 | Fischell et al. |
| 4,800,882 A | 1/1989 | Gianturco |
| 4,852,568 A | 8/1989 | Kensey |
| 4,856,516 A | 8/1989 | Hillstead |
| 4,941,870 A | 7/1990 | Okada et al. |
| 4,990,582 A | 2/1991 | Salamone |
| 4,994,069 A | 2/1991 | Ritchart et al. |
| 5,015,253 A | 5/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,041,126 A | 8/1991 | Gianturco |
| 5,041,292 A | 8/1991 | Feijen |
| 5,078,726 A | 1/1992 | Kreamer |
| 5,084,065 A | 1/1992 | Weldon et al. |
| 5,116,365 A | 5/1992 | Hillstead |
| 5,133,731 A | 7/1992 | Butler et al. |
| 5,135,536 A | 8/1992 | Hillstead |
| 5,158,548 A | 10/1992 | Lau et al. |
| 5,162,430 A | 11/1992 | Rhee et al. |
| 5,171,262 A | 12/1992 | MacGregor |
| 5,192,297 A | 3/1993 | Hull |
| 5,197,978 A | 3/1993 | Hess |
| 5,226,911 A | 7/1993 | Chee et al. |
| 5,234,456 A | 8/1993 | Silvestrini |
| 5,256,146 A | 10/1993 | Andrews |
| 5,258,042 A | 11/1993 | Mehta |
| 5,304,200 A | 4/1994 | Spaulding |
| 5,312,415 A | 5/1994 | Palermo |
| 5,314,444 A | 5/1994 | Gianturco |
| 5,342,300 A | 8/1994 | Stefanadis |
| 5,382,259 A | 1/1995 | Phelps et al. |
| 5,382,260 A | 1/1995 | Dormandy, Jr. et al. |
| 5,383,887 A | 1/1995 | Nadal |
| 5,389,106 A | 2/1995 | Tower |
| 5,395,390 A | 3/1995 | Simon et al. |
| 5,405,377 A | 4/1995 | Cragg |
| 5,410,016 A | 4/1995 | Hubbell et al. |
| 5,415,664 A | 5/1995 | Pinchuk |
| D359,802 S | 6/1995 | Fontaine |
| 5,433,723 A | 7/1995 | Lindenberg et al. |
| 5,464,449 A | 11/1995 | Fogarty |
| 5,476,472 A | 12/1995 | Dormandy, Jr. et al. |
| 5,476,505 A | 12/1995 | Limon |
| 5,480,423 A | 1/1996 | Ravenscroft et al. |
| 5,484,449 A | 1/1996 | Amundson et al. |
| 5,514,379 A | 5/1996 | Weissleder et al. |
| 5,514,380 A | 5/1996 | Song et al. |
| 5,536,274 A | 7/1996 | Neuss |
| 5,540,701 A | 7/1996 | Erlich |
| 5,554,190 A | 9/1996 | Draenert |
| 5,558,633 A | 9/1996 | Phipps et al. |
| 5,578,074 A | 11/1996 | Mirigian |
| 5,582,619 A | 12/1996 | Ken |
| 5,607,445 A | 3/1997 | Summers |
| 5,609,627 A | 3/1997 | Goicoechea et al. |
| 5,609,628 A | 3/1997 | Keranen |
| 5,609,629 A | 3/1997 | Fearnot et al. |
| 5,613,981 A | 3/1997 | Boyle et al. |
| 5,624,461 A | 4/1997 | Mariant |
| 5,630,829 A | 5/1997 | Lauterjung |
| 5,645,558 A | 7/1997 | Horton |
| 5,658,308 A | 8/1997 | Snyder |
| 5,674,241 A | 10/1997 | Bley et al. |
| 5,674,276 A | 10/1997 | Andersen et al. |
| 5,674,295 A | 10/1997 | Ray et al. |
| 5,702,418 A | 12/1997 | Ravenscroft |
| 5,716,410 A | 2/1998 | Wang et al. |
| 5,718,711 A | 2/1998 | Berenstein et al. |
| 5,741,325 A | 4/1998 | Chaikof et al. |
| 5,749,894 A | 5/1998 | Engelson |
| 5,750,585 A | 5/1998 | Park et al. |
| 5,769,882 A | 6/1998 | Fogarty et al. |
| 5,785,679 A | 7/1998 | Abolfathi et al. |
| 5,785,965 A | 7/1998 | Pratt et al. |
| 5,800,454 A | 9/1998 | Jacobsen et al. |
| 5,823,198 A | 10/1998 | Jones et al. |
| 5,843,089 A | 12/1998 | Sahatjian et al. |
| 5,898,062 A | 4/1999 | Allcock et al. |
| 5,911,717 A | 6/1999 | Jacobsen et al. |
| 5,911,731 A | 6/1999 | Pham et al. |
| 5,919,224 A | 7/1999 | Thompson et al. |
| 5,935,148 A | 8/1999 | Villar et al. |
| 5,941,249 A | 8/1999 | Maynard |
| 5,951,599 A | 9/1999 | McCrory |
| 5,980,514 A | 11/1999 | Kupiecki et al. |
| 5,980,550 A | 11/1999 | Eder |
| 5,980,554 A | 11/1999 | Lenker et al. |
| 5,990,237 A | 11/1999 | Bentley et al. |
| 6,015,431 A | 1/2000 | Thornton et al. |
| 6,036,720 A | 3/2000 | Abrams et al. |
| 6,053,940 A | 4/2000 | Wijay |
| 6,060,534 A | 5/2000 | Ronan et al. |
| 6,063,070 A | 5/2000 | Eder et al. |
| 6,063,111 A | 5/2000 | Hieshima et al. |
| 6,086,577 A | 7/2000 | Ken et al. |
| 6,090,911 A | 7/2000 | Petka et al. |
| 6,093,199 A | 7/2000 | Brown et al. |
| 6,113,629 A | 9/2000 | Ken |
| 6,120,847 A | 9/2000 | Yang et al. |
| 6,140,127 A | 10/2000 | Sprague |
| 6,143,022 A | 11/2000 | Shull et al. |
| 6,152,144 A | 11/2000 | Lesh et al. |
| 6,165,193 A | 12/2000 | Greene, Jr. et al. |
| 6,165,194 A | 12/2000 | Denardo et al. |
| 6,168,592 B1 | 1/2001 | Kupiecki et al. |
| 6,168,615 B1 | 1/2001 | Ken et al. |
| 6,176,240 B1 | 1/2001 | Nikolchev et al. |
| 6,177,095 B1 | 1/2001 | Sawhney et al. |
| 6,184,266 B1 | 2/2001 | Ronan et al. |
| 6,187,370 B1 | 2/2001 | Dinh et al. |
| 6,190,402 B1 | 2/2001 | Horton et al. |
| 6,193,708 B1 | 2/2001 | Ken et al. |
| 6,201,065 B1 | 3/2001 | Pathak et al. |
| 6,221,099 B1 | 4/2001 | Andersen et al. |
| 6,224,892 B1 | 5/2001 | Searle |
| 6,231,597 B1 | 5/2001 | Deem |
| 6,261,305 B1 | 7/2001 | Marotta et al. |
| 6,264,695 B1 | 7/2001 | Stoy |
| 6,268,161 B1 | 7/2001 | Han et al. |
| 6,273,908 B1 | 8/2001 | Ndondo-Lay |
| 6,280,457 B1 | 8/2001 | Wallace et al. |
| 6,287,318 B1 * | 9/2001 | Villar ............... A61B 17/12022 606/191 |
| 6,287,333 B1 | 9/2001 | Appling et al. |
| 6,309,367 B1 | 10/2001 | Boock |
| 6,360,129 B1 | 3/2002 | Ley et al. |
| 6,364,893 B1 | 4/2002 | Sahatjian et al. |
| 6,383,174 B1 | 5/2002 | Eder |
| 6,398,808 B1 | 6/2002 | Palasis |
| 6,419,686 B1 | 7/2002 | McLeod et al. |
| 6,551,303 B1 | 4/2003 | Van Tassel et al. |
| 6,554,849 B1 | 4/2003 | Jones et al. |
| 6,569,179 B2 | 5/2003 | Teoh et al. |
| 6,569,190 B2 | 5/2003 | Whalen, II et al. |
| 6,582,460 B1 | 6/2003 | Cryer |
| 6,596,296 B1 | 7/2003 | Nelson et al. |

(56) References Cited

U.S. PATENT DOCUMENTS

| | | | |
|---|---|---|---|
| 6,605,111 B2 | 8/2003 | Bose et al. | |
| 6,605,294 B2 | 8/2003 | Sawhney | |
| 6,613,073 B1 | 9/2003 | White et al. | |
| 6,613,074 B1 | 9/2003 | Mitelberg et al. | |
| 6,663,607 B2 | 12/2003 | Slaikeu et al. | |
| 6,712,836 B1 * | 3/2004 | Berg et al. | 606/213 |
| 6,716,445 B2 | 4/2004 | Won et al. | |
| 6,723,108 B1 | 4/2004 | Jones et al. | |
| 6,746,468 B1 | 6/2004 | Sepetka et al. | |
| 6,748,953 B2 | 6/2004 | Sherry et al. | |
| 6,786,876 B2 | 9/2004 | Cox | |
| 6,811,560 B2 | 11/2004 | Jones et al. | |
| 6,818,013 B2 | 11/2004 | Mitelberg et al. | |
| 6,878,384 B2 | 4/2005 | Cruise et al. | |
| 6,932,833 B1 | 8/2005 | Sandoval et al. | |
| 7,018,403 B1 | 3/2006 | Pienknagura | |
| 7,037,331 B2 | 5/2006 | Mitelberg et al. | |
| 7,195,648 B2 | 3/2007 | Jones et al. | |
| 7,241,301 B2 | 7/2007 | Thramann | |
| 7,300,661 B2 | 11/2007 | Henson et al. | |
| 7,311,726 B2 | 12/2007 | Mitelberg et al. | |
| 7,361,367 B2 | 4/2008 | Henson et al. | |
| 7,371,228 B2 | 5/2008 | Chu et al. | |
| 7,396,540 B2 | 7/2008 | Chu et al. | |
| 7,442,382 B2 | 10/2008 | Henson et al. | |
| 7,481,821 B2 | 1/2009 | Fogarty | |
| 7,517,361 B1 | 4/2009 | Ravenscroft | |
| 7,530,988 B2 | 5/2009 | Evans et al. | |
| 7,569,066 B2 | 8/2009 | Gerberding et al. | |
| 7,572,288 B2 | 8/2009 | Cox | |
| 7,582,109 B2 | 9/2009 | Delegge | |
| 7,666,220 B2 | 2/2010 | Evans et al. | |
| 7,790,273 B2 | 9/2010 | Lee et al. | |
| 7,815,661 B2 | 10/2010 | Mirizzi et al. | |
| 7,862,538 B2 | 1/2011 | Sawhney et al. | |
| 7,951,448 B2 | 5/2011 | Lee et al. | |
| 7,959,676 B2 | 6/2011 | Thramann et al. | |
| 8,048,145 B2 | 11/2011 | Evans et al. | |
| 8,075,585 B2 | 12/2011 | Lee et al. | |
| 8,105,352 B2 | 1/2012 | Egnelov | |
| 8,182,525 B2 | 5/2012 | Herbowy et al. | |
| 8,231,666 B2 | 7/2012 | Kim et al. | |
| 8,231,890 B2 | 7/2012 | Cruise et al. | |
| 8,252,040 B2 | 8/2012 | Cox | |
| 8,262,686 B2 | 9/2012 | Fogarty | |
| 8,317,799 B2 * | 11/2012 | Schon | A61B 17/0057 606/92 |
| 8,333,798 B2 | 12/2012 | Gandhi et al. | |
| 8,465,779 B2 | 6/2013 | Cruise et al. | |
| 8,486,046 B2 | 7/2013 | Hayman et al. | |
| 8,535,367 B2 | 9/2013 | Kim et al. | |
| 8,562,341 B2 | 10/2013 | Luebke | |
| 8,562,636 B2 | 10/2013 | Fogarty | |
| 8,562,643 B2 | 10/2013 | Tekulve et al. | |
| 8,562,662 B2 | 10/2013 | Kim et al. | |
| 8,585,723 B2 | 11/2013 | Nardone et al. | |
| 8,597,674 B2 | 12/2013 | Chu et al. | |
| 8,636,764 B2 | 1/2014 | Miles et al. | |
| 8,647,377 B2 | 2/2014 | Kim et al. | |
| 2001/0000188 A1 | 4/2001 | Lenker et al. | |
| 2001/0000797 A1 | 5/2001 | Mazzocchi et al. | |
| 2001/0012961 A1 | 8/2001 | Deem | |
| 2001/0025195 A1 | 9/2001 | Shaolian et al. | |
| 2001/0047202 A1 | 11/2001 | Slaikeu | |
| 2002/0013618 A1 | 1/2002 | Marotta | |
| 2002/0026228 A1 | 2/2002 | Schauerte | |
| 2002/0026232 A1 | 2/2002 | Marotta | |
| 2002/0049495 A1 | 4/2002 | Kutryk | |
| 2002/0052648 A1 | 5/2002 | Mcguckin | |
| 2002/0123789 A1 | 9/2002 | Francis | |
| 2002/0143349 A1 | 10/2002 | Gifford et al. | |
| 2002/0169473 A1 | 11/2002 | Sepetka et al. | |
| 2003/0004531 A1 | 1/2003 | Jones | |
| 2003/0018294 A1 | 1/2003 | Cox | |
| 2003/0023190 A1 | 1/2003 | Cox | |
| 2003/0055451 A1 | 3/2003 | Jones | |
| 2003/0120300 A1 | 6/2003 | Porter | |
| 2003/0135266 A1 | 7/2003 | Chew et al. | |
| 2003/0135267 A1 | 7/2003 | Solem | |
| 2003/0139802 A1 | 7/2003 | Wulfman | |
| 2003/0139806 A1 | 7/2003 | Haverkost et al. | |
| 2003/0171739 A1 | 9/2003 | Murphy | |
| 2004/0034386 A1 | 2/2004 | Fulton | |
| 2004/0044351 A1 | 3/2004 | Searle | |
| 2004/0087998 A1 | 5/2004 | Lee et al. | |
| 2004/0093076 A1 | 5/2004 | White | |
| 2004/0098027 A1 | 5/2004 | Teoh et al. | |
| 2004/0106945 A1 | 6/2004 | Thramann | |
| 2004/0111112 A1 | 6/2004 | Hoffmann | |
| 2004/0172056 A1 | 9/2004 | Guterman | |
| 2004/0186562 A1 | 9/2004 | Cox | |
| 2004/0193206 A1 | 9/2004 | Gerberding | |
| 2005/0033409 A1 | 2/2005 | Burke | |
| 2005/0090856 A1 * | 4/2005 | Porter | 606/200 |
| 2005/0283962 A1 * | 12/2005 | Boudjemline | A61B 17/0057 29/433 |
| 2006/0009798 A1 | 1/2006 | Callister et al. | |
| 2006/0052820 A1 * | 3/2006 | Haig | A61B 17/12172 606/213 |
| 2006/0122685 A1 | 6/2006 | Bonsignore et al. | |
| 2006/0206201 A1 | 9/2006 | Garcia et al. | |
| 2007/0078479 A1 * | 4/2007 | Belenkaya et al. | 606/200 |
| 2007/0148243 A1 * | 6/2007 | Bates | A61K 9/0019 424/484 |
| 2007/0179590 A1 | 8/2007 | Lu et al. | |
| 2007/0207186 A1 | 9/2007 | Scanlon et al. | |
| 2007/0227544 A1 | 10/2007 | Swann et al. | |
| 2007/0276465 A1 | 11/2007 | Mongrain | |
| 2007/0276470 A1 | 11/2007 | Tenne | |
| 2007/0299464 A1 | 12/2007 | Cruise et al. | |
| 2008/0109063 A1 | 5/2008 | Hancock et al. | |
| 2008/0208167 A1 | 8/2008 | Stankus | |
| 2008/0221671 A1 | 9/2008 | Chouinard et al. | |
| 2009/0056722 A1 | 3/2009 | Swann | |
| 2009/0099643 A1 | 4/2009 | Hyodoh et al. | |
| 2009/0177221 A1 | 7/2009 | Kramann | |
| 2009/0177264 A1 | 7/2009 | Ravenscroft | |
| 2009/0182371 A1 | 7/2009 | Clausen et al. | |
| 2009/0198315 A1 | 8/2009 | Boudjemline | |
| 2009/0232869 A1 | 9/2009 | Greene, Jr. | |
| 2009/0254176 A1 | 10/2009 | Butera | |
| 2009/0287145 A1 | 11/2009 | Cragg et al. | |
| 2009/0287297 A1 | 11/2009 | Cox | |
| 2009/0287300 A1 | 11/2009 | Dave et al. | |
| 2010/0262177 A1 | 10/2010 | Frigstad et al. | |
| 2011/0066221 A1 | 3/2011 | White et al. | |
| 2011/0245802 A1 | 10/2011 | Hayman et al. | |
| 2012/0095501 A1 | 4/2012 | Nardone et al. | |
| 2012/0101519 A1 | 4/2012 | Hill et al. | |
| 2012/0118445 A1 | 5/2012 | Luebke | |
| 2012/0271348 A1 | 10/2012 | Tekulve | |
| 2012/0272526 A1 | 11/2012 | Luebke | |

FOREIGN PATENT DOCUMENTS

| | | |
|---|---|---|
| EP | 0518704 A1 | 12/1992 |
| EP | 0627201 A1 | 12/1994 |
| EP | 0664104 A2 | 7/1995 |
| EP | 0717969 A2 | 6/1996 |
| EP | 1266631 A1 | 12/2002 |
| EP | 1691881 A2 | 5/2005 |
| EP | 1732467 A1 | 12/2006 |
| EP | 2105110 A1 | 9/2009 |
| GB | 2139898 A | 11/1984 |
| WO | WO1989011257 A1 | 11/1989 |
| WO | WO1992014408 A1 | 8/1992 |
| WO | WO1994016629 A1 | 8/1994 |
| WO | WO1995018585 A1 | 7/1995 |
| WO | WO1995/032018 A1 | 11/1995 |
| WO | WO1997042910 A1 | 11/1997 |
| WO | WO1998004198 A1 | 2/1998 |
| WO | WO1998050102 A1 | 11/1998 |
| WO | WO1998/058590 A1 | 12/1998 |
| WO | WO1999002092 A1 | 1/1999 |

(56) References Cited

FOREIGN PATENT DOCUMENTS

| WO | WO1999005977 A1 | 2/1999 |
| --- | --- | --- |
| WO | WO1999007293 A1 | 2/1999 |
| WO | WO1999059479 A1 | 11/1999 |
| WO | WO1999062429 A1 | 12/1999 |
| WO | WO1999062432 A1 | 12/1999 |
| WO | WO1999065397 A1 | 12/1999 |
| WO | WO2000004845 A2 | 2/2000 |
| WO | WO2000007524 A1 | 2/2000 |
| WO | WO2000013593 A1 | 3/2000 |
| WO | WO2000018321 A1 | 4/2000 |
| WO | WO2000027292 A1 | 5/2000 |
| WO | WO2000032112 A1 | 6/2000 |
| WO | WO2000044306 A1 | 8/2000 |
| WO | WO2000056247 A1 | 9/2000 |
| WO | WO2000057818 A1 | 10/2000 |
| WO | WO2000062711 A1 | 10/2000 |
| WO | WO2000074577 A1 | 12/2000 |
| WO | WO2001001890 A1 | 1/2001 |
| WO | WO2001003607 A2 | 1/2001 |
| WO | WO2001037892 A1 | 5/2001 |
| WO | WO2001041676 A1 | 6/2001 |
| WO | WO2001093780 A2 | 12/2001 |
| WO | WO2002005731 A1 | 1/2002 |
| WO | WO2002080782 A1 | 10/2002 |
| WO | WO2002087472 A1 | 11/2002 |
| WO | WO2003077984 A1 | 9/2003 |
| WO | WO2006081407 A1 | 8/2006 |
| WO | WO2007028452 A1 | 3/2007 |
| WO | WO2007062661 A2 | 6/2007 |
| WO | WO2008/115922 A1 | 9/2008 |
| WO | WO2009003049 A2 | 12/2008 |
| WO | WO2009096991 A1 | 8/2009 |
| WO | WO2009132141 A1 | 10/2009 |
| WO | WO2011084536 A2 | 7/2011 |
| WO | WO2013184595 A1 | 12/2013 |

OTHER PUBLICATIONS

Balt Extrusion, Montmorency, Francy, "LEO+," Intracranial self expandable stent and delivery system, product page.

WIPO, U.S. International Search Authority, International Search Report and Written Opinion dated Oct. 22, 2012 in International Patent Application No. PCT/US2012/037621, 10 pages.

WIPO, U.S. International Search Authority, International Search Report and Written Opinion dated Mar. 7, 2011 in International Patent Application No. PCT/US2010/061627, 9 pages.

Han, Y.M. et al., "Flared Polyurethane-covered Self-expandable Nitinol Stent for Malignant Biliary Obstruction," *J Vasc Interv Radiol*, Oct. 2003; 14 (10): pp. 1291-1301.

Lieber, B.B. et al., "Alteration of Hemodynamics in Aneurysm Models by Stenting. Influence of Stent Porosity," *Annals of Biomedical Engineering*, 1997, vol. 25, pp. 460-469.

Duprat G. Jr., et al., "Self Expanding Evaluation", Radiology 1987; 162: 469-472.

Guglielmi G., et al., "Electrothrombosis of Results", J. Neurosurg. 1991; 75: 1-7.

Guglielmi G., et al., "Electrothrombosis of saccular aneurysms via endovascular approach", J. Neurosurg. 1991; 75: 8-14.

Hieshima G. B. et al., "A Detachable Occlusion", Radiology 1981; 138: 227-228.

Paper No. 199, American Society of Neuroradiology, 29th Annual Meeting, Washington, D.C., Jun. 9-14, 1991.

Paper No. 200, American Society of Neuroradiology, 29th Annual Meeting, Washington, D.C., Jun. 9-14, 1991.

Romodanov A. P., et al., Intravascular Occlusion Catheter, In Advances & Technical Standards, vol. 9, 1982; 25 49.

Serbinenko F. A. "Balloon Catheterization and Cerebral Vessels", J. Neurosurg. 1974; 41: 125-145.

Sigwart V., et al., Intravascular Angioplasty, N. England J. Med., 1987; 316: 701 706.

Strecker E. P., "Flexible, Balloon Results", Radiology 1988; 169: 388.

Ahuja, A.A., Hergenrother, R. W., Strother, C.M., Rappe, A.A., Cooper, S.L., and Graves, V.B., "Platinum Coil Coatings to Increase Thrombogenicity: A Preliminary Study in Rabbits," AJNR 14:794-798, Jul./Aug. 1993.

Dawson, R., M.D., Krisht, A., M.D., Barrow, D., M.D., Joseph, G., M.D., Shengelaia, G., M.D., and Bonner, G., M.B.A., "Treatment of Experimental Aneurysms Using Collagen-Coated Microcoils," Neurosurgery, 36:133-140, 1995.

Vinuela, F., M.D., Duckwiler, G., M.D., and Mawad, M., M.D., "Guglielmi Detachable Coil Emoblization of Acute Intracranial Aneurysm: Perioperative Anatomical and Clinical Outcome in 403 Patients," J. Neurosurg 86:475-482, 1997.

* cited by examiner

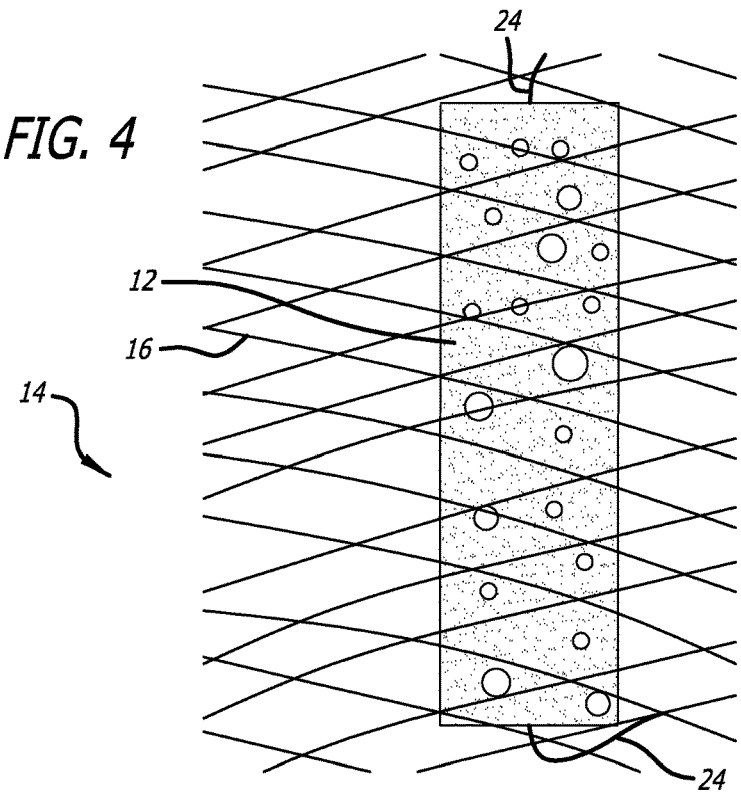
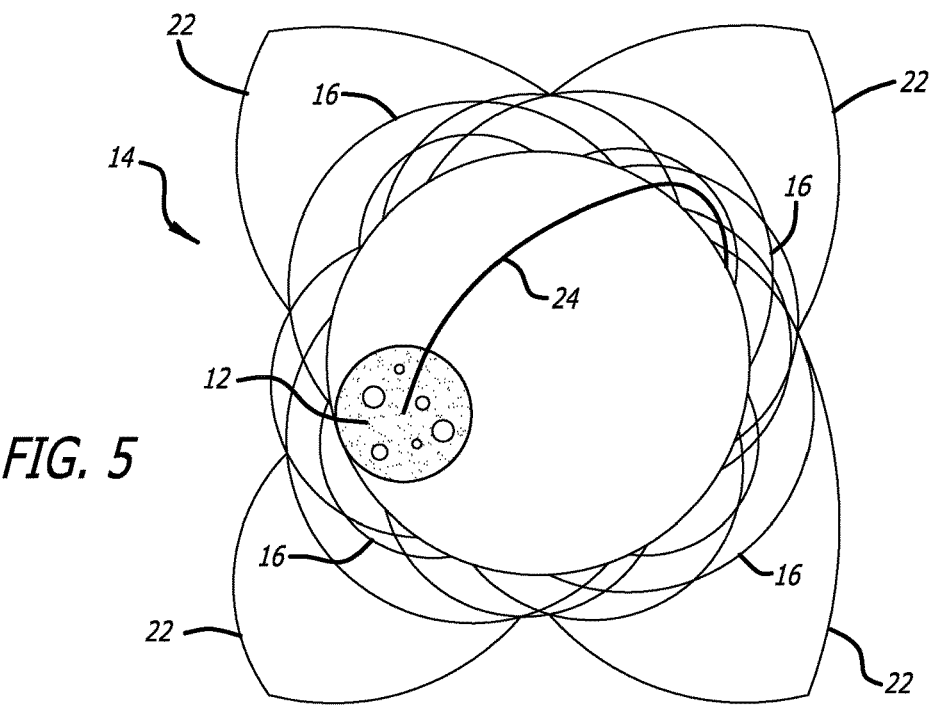

DEVICE FOR OCCLUDING A LUMEN

RELATED APPLICATIONS

This application claims priority to U.S. Provisional Patent Application Ser. No. 61/485,065 filed May 11, 2011 entitled Device for Occluding A Lumen, the entirety of which is incorporated by reference herein.

FIELD OF THE INVENTION

The present invention is directed to devices for occluding lumens within a body and, more particularly, directed to devices employing an expansile frame associated with an expansile plug and methods for use and manufacturing of such devices.

BACKGROUND OF THE INVENTION

It is often necessary to close a blood vessel, lumen, duct, aneurysm, hole, fistula, or appendage, referred to herein collectively as a lumen, within a body. For example, under certain circumstances the optimum treatment for an aneurysm is to occlude the vessel that feeds blood into the lesion. In the neurovascular anatomy, this vessel may be the carotid artery, or in the peripheral vasculature, it may be an iliac artery. Additional examples include: a patent ductus arteriosus (PDA) which shunts blood from the aorta to the pulmonary artery in some newborn babies; a patent foramen ovale (PFO), an open flap in the septum separating the heart's atria; a blood vessel feeding a tumor; an atrial septal defect (ASD), a hole in the septum between the atria; an iliac artery in conjunction with a stent graft and a femoral-femoral bypass operation the closure of which provides treatment of an aortic aneurysm; an atrial appendage, which is a malformation that allows blood clots to collect, which, in turn, may cause a stroke. Furthermore, there are various types of fistula in which organs are improperly connected together such as colovaginal fistula, oromaxillary fistula, and arteriovenous malformation (AVM).

There are numerous devices in the prior art that may be used to close or otherwise occlude these lumens. One such device is a detachable balloon which is inflated in the target lumen with a liquid or polymer, then detached and maintained at or in the target. Another device is a basket-like structure formed of wires that causes clots in the blood flow thereby blocking a blood vessel. Another device is a coil or hydrogel coated coil that is deployed in a lumen. Another device is a self-expanding patch that blocks a PFO or ASD from both sides. Further examples include plugs, beads, or particles made from hydrogel or polyvinyl alcohol (PVA) that may expand upon blood contact and serve to occlude or block a lumen.

There is, however, an ongoing need to provide a more advanced and improved device for occluding lumens that is easier to place, requires fewer steps for deployment, and has a lower tendency to migrate after placement.

SUMMARY OF THE INVENTION

One embodiment according to the present invention includes an occlusion device in which the support structure or frame expands circumferentially within the lumen to secure an expansile plug or embolic material. Once in place, the expansile plug or embolic material expands, thereby occluding the target lumen.

Another embodiment according to the present invention includes a radially expandable support structure having a closed portion for capturing subsequently delivered embolic material, such as embolic coils. For example, the structure may have a closed portion at its distal end or at its middle (forming an hourglass shape). Additionally, the closed portion may be formed from the support structure itself or from a discrete, second layer that is attached within the support structure.

The occlusion devices of the present invention can be useful in multiple medical fields such as radiology, gastroenterology, gynecology, cardiology, neurovascular intervention, and oncology.

BRIEF DESCRIPTION OF THE DRAWINGS

These and other aspects, features, and advantages of which embodiments of the invention are capable of will be apparent and elucidated from the following description of embodiments of the present invention, reference being made to the accompanying drawings, in which

FIG. 4 is a side elevation view of a portion of a device according to one embodiment of the present invention;

FIG. 5 is a plan view of a portion of a device according to one embodiment of the present invention;

DETAILED DESCRIPTION OF THE EMBODIMENTS

Figure 1:
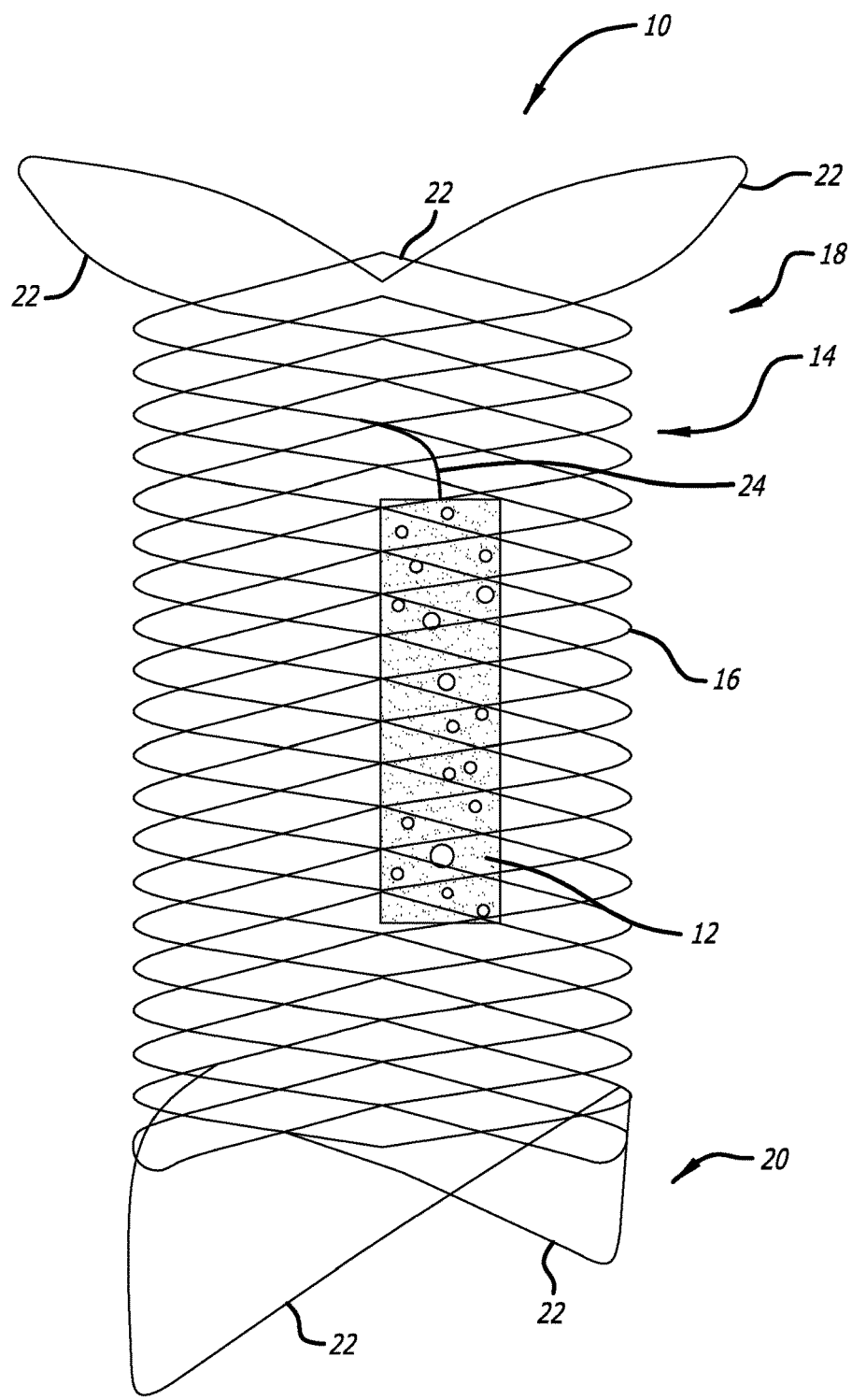
FIG. 1 is a side elevation view of a portion of a device according to one embodiment of the present invention.
Figure 2:
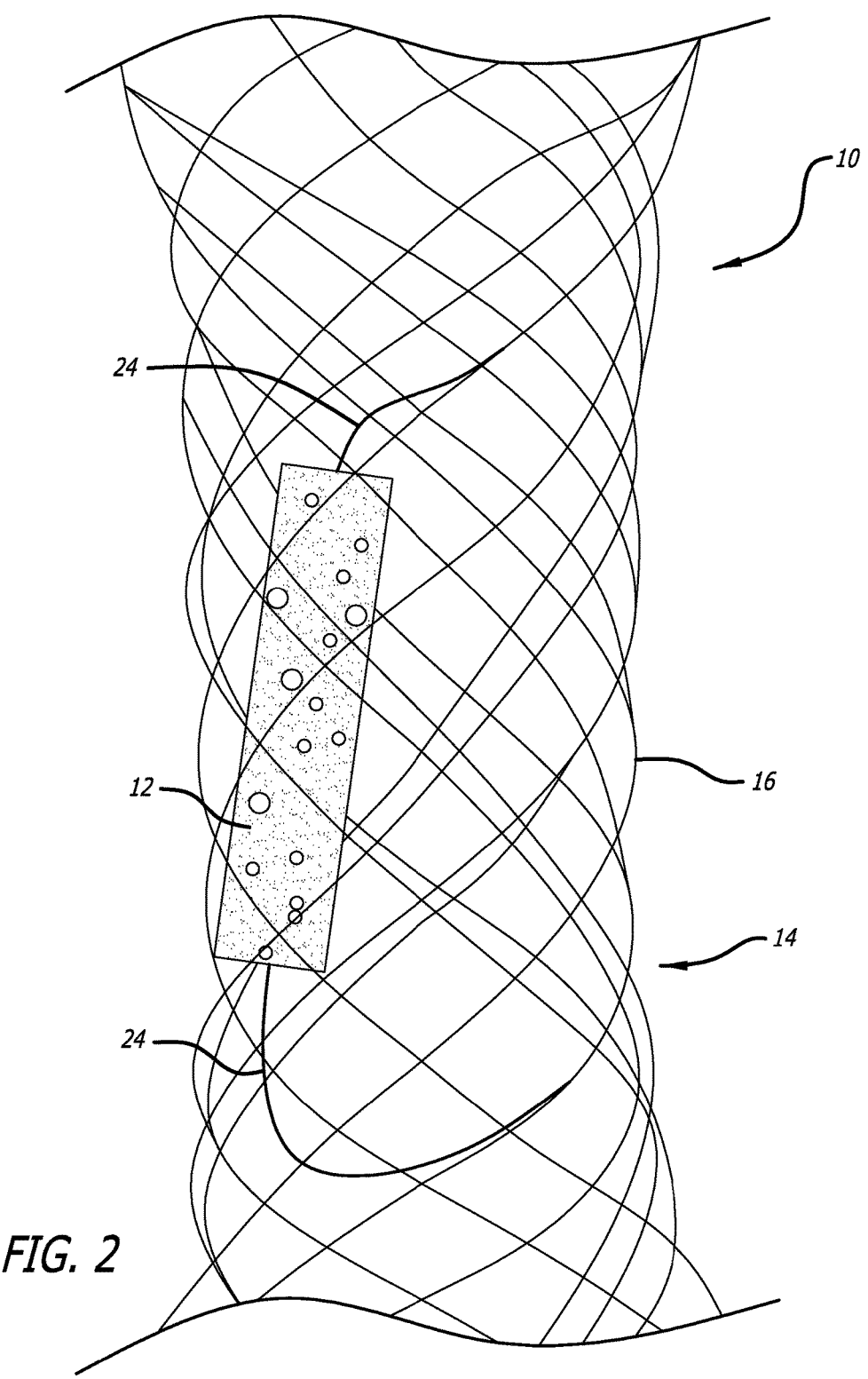
FIG. 2 is a side elevation view of a portion of a device according to one embodiment of the present invention.
Figure 3:
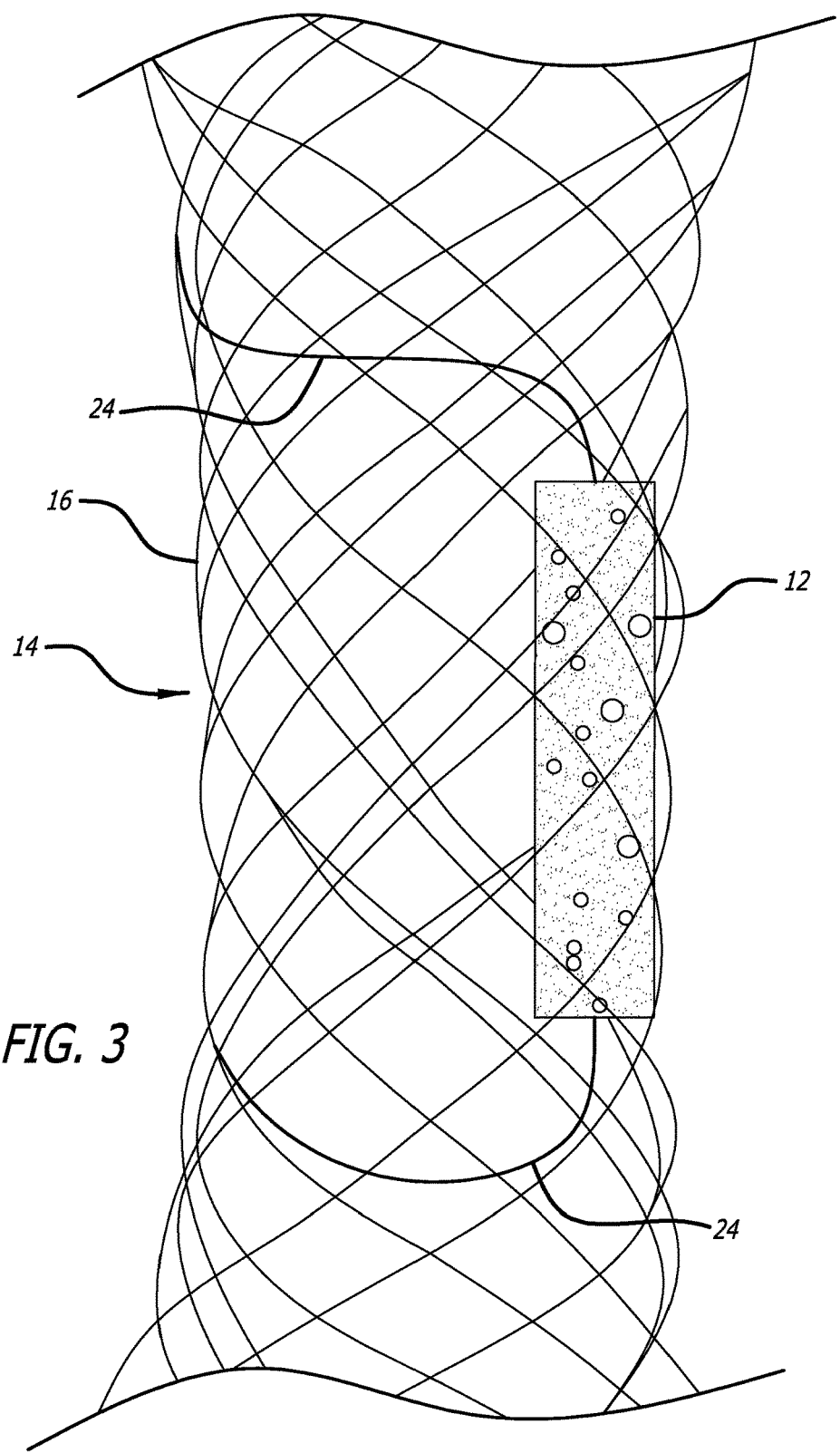
FIG. 3 is a side elevation view of a portion of a device according to one embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The embodiments of the present invention are generally directed to lumen occlusion devices having an expandable framework. As described in more detail below, the framework may have an attached, expansile plug or may be filled with embolic material after deployment.

FIGS. 1-5 illustrate a device 10 according to the present invention, which employs one or more expandable plug 12 associated with a frame or support structure 14. The frame 14 is preferably formed of a single wire 16 braided or woven into a generally tubular form but can also be formed by weaving multiple, discrete wires or laser cutting a tube. In one example, the frame 14 has an external diameter of approximately 4.5 millimeters and a length of approximately 15 millimeters. The wire 16 is preferably formed of NiTi or nickel-titanium alloy, also known as Nitinol, having a diameter of approximately 0.00325 inches.

The frame 14 has a proximal end portion 18 and a distal end portion 20 that are outwardly flared. Alternatively stated, the proximal end portion 18 and the distal end portion 20 employ projecting elements 22 extending radially outward. In certain embodiments, the projecting elements 22 take the form of loops, hooks, protuberances, or staples, which tend to increase the friction between the frame and the lumen. These projecting elements 22 tend to hold the frame 14 in place in conjunction with the frame's 14 radial force. This feature is especially useful when the area or lumen to be obstructed is relatively short, which reduces the aggregate radial force of the frame 14 compared to a longer lumen, or where there is high flow such as an iliac or carotid artery.

In certain embodiments, a variety of radiopaque markers such as marker bands, coils, and plating, not shown, are connected to the frame 14. For example, markers can be located at the ends of the projecting elements 22, near the plug 12, and/or along a length of the frame 14 to assist the operator with visualization, guidance and delivery of the device 10 during deployment.

Formation of the relaxed or minimum energy state configuration of shape memory structures such as the device 10 described herein are well known in the art. For example, the relaxed or minimum energy state configuration of the frame 14 is formed by weaving, winding, or otherwise manipulating the wire 16 about a fixture. Once the desired form is achieved for the frame 14, the frame 14 is subjected to a heat treatment. For example, the frame 14 is maintained at a temperature of about 500 degrees Celsius to about 1000 degrees Celsius for approximately 30 to 90 minutes. Following the heat treatment, the frame 14 is cooled to room temperature and ultrasonically cleaned. The resultant secondary configuration is thereby made permanent and becomes the relaxed or minimum energy state configuration of the device 10.

In one embodiment, the frame 14 is formed of a plurality of the same or a combination of different wires 18. For example, the wire 16 may be formed of Nitinol, steel, chromium-cobalt alloy, and/or platinum, and/or of polymers such as Teflon, polyethylene terephthalate (PET), or polyether ether ketone (PEEK).

In one embodiment, the frame 14 can be any of the stents seen in U.S. application Ser. No. 13/003,277 filed Jan. 7, 2011 and U.S. application Ser. No. 13/311,430 filed Dec. 5, 2011, the contents of which are hereby incorporated by reference.

The plug 12 is formed of, for example, hydrogel or other similar expansile material such as PVA or hydrogel foam. As shown in FIGS. 1-5, the plug 12 is preferably formed in the shape of a cylinder that expands after being introduced into a patient. In a reduced or non-expanded state, the plug 12 preferably has a diameter of approximately 1 millimeter and a length of approximately 7 millimeters. In an expanded, unrestricted state (for example, caused by exposure of the plug 12 to water or blood), the plug 12 preferably has a diameter of approximately 4 millimeters and a length of approximately 14 millimeters.

The plug 12 can be constructed from a variety of known polymeric materials including, for example, biocompatible, macroporous or microporous, hydrophilic or hydrophobic hydrogel foam materials. Suitable materials are described in U.S. Pat. No. 6,165,193 to Greene Jr. et al. and U.S. Pat. No. 6,878,384 to Cruise et al., each of which is hereby incorporated by reference. The plug 12 may also comprise polymers such as polyvinyl alcohol foams as described in U.S. Pat. No. 5,823,198 to Jones et al., which is also incorporated herein by reference.

In another embodiment of the present invention, the plug 12 is made of a biocompatible, macroporous, hydrophilic hydrogel foam material, in particular a water-swellable foam matrix formed as a macroporous solid comprising a foam stabilizing agent and a polymer or copolymer of a free radical polymerizable hydrophilic olefin monomer cross-linked with up to about 10% by weight of a multiolefin-functional cross-linking agent. A suitable material of this type is described in U.S. Pat. No. 5,750,585 to Park et al., the disclosure of which is incorporated herein by reference. Another suitable material is a porous hydrated polyvinyl alcohol foam (PAF) gel prepared from a polyvinyl alcohol solution in a mixed solvent consisting of water and a water-miscible organic solvent, as described, for example, in U.S. Pat. No. 4,663,358 to Hyon et al., the disclosure of which is incorporated herein by reference. Still another suitable material is PHEMA, as discussed in U.S. Pat. No. 4,663,358 to Hyon et al., "Hydrolysed Microspheres from Cross-Linked Polymethyl Methacrylate", J. Neuroradiol., Vol. 18, pp. 61-69 (1991), both of which are hereby incorporated by reference.

It may be desirable to reduce the size of the plug 12 for the purpose of performing percutaneous procedures. This may be done mechanically by using a fixture to compress the plug, chemically by dehydrating the polymer with an agent such as alcohol, or through a combination of these methods. I In certain embodiments of the present invention, the plug 12 may incorporate radiopaque elements, for example, iodine or tantalum powder, mixed into the material forming the plug 12 during manufacturing to help visualize the location of the plug 12 and the device 10 before and after deployment.

The plug 12 is preferably associated with or otherwise attached to the frame 14 by a thread 24. The thread 24 is formed of, for example, polyethylene terephthalate (PET) having a diameter of approximately 0.0009 inches. One end of the thread 24 is skewered or otherwise passed through a portion of the plug 12 and around the wire 16 of the frame 14 and then fixed to a second end of the thread 24 so as to form a loop. A plurality of threads 24 may also be employed to secure the plug 12 to the frame 14 at the same or at different locations along a dimension of the frame 14.

In certain embodiments, the plug 12 is associated with the frame 14 by employing a thread 24 formed of polypropylene or olefin elastomer such as Engage. Still in other embodiments, the plug 12 is associated with the frame 14 by mechanical methods such as: constructing the frame 14 in the shape of a cage or basket that holds the plug 12 within; directly skewering an element of the frame 14, such as a portion of the wire 16, through the plug 12; gluing the plug to the frame 14; incorporating mechanical grasping elements into the frame 14 to hold the plug 12; or using heat-shrinkable plastic to hold the plug 12 to the frame 14.

After the frame 14 and plug 12 have been associated, the device 10 can be loaded into a delivery device such as a catheter or sheath. In a more specific example, the device 10 can be compressed on an inner pusher member that is located within a retractable sheath. In one example, the delivery device has a size of about 4 French for delivery into a lumen or vessel between about 2-4 millimeters in diameter.

Figure 6:
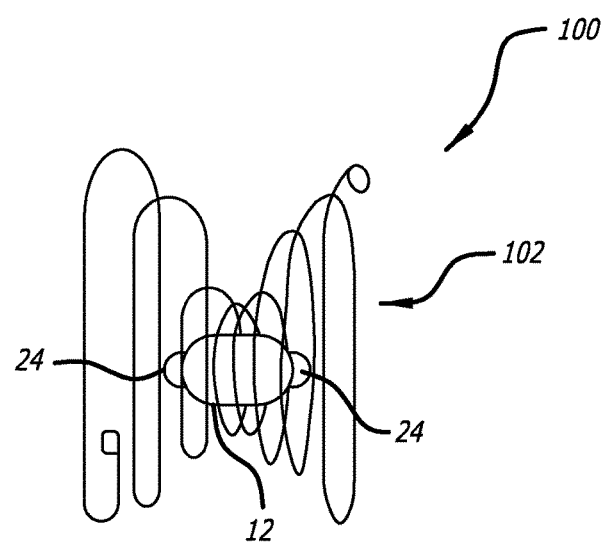
FIG. 6 is a side elevation view of a device according to one embodiment of the present invention.

FIG. 6 illustrates another embodiment of a device 100 having a generally "hourglass" shaped side-profile. More specifically, the device 100 includes a frame 102, preferably composed of a single wire that forms a spiral or a substantially planar helix. Loops of the frame 102 have a generally smaller diameter at a middle region of the frame 102 and increase in diameter towards the distal and proximal ends of the frame 102.

One or more plugs 12 are attached at the narrow, center portion of the frame 102 as described in previous embodiments, for example by employing threads 24. Alternatively, one or more plugs 12 may be anchored to the frame 102 by skewering the plugs 12 with the frame 102. Radiopaque markers, not shown, may also be employed as previously described regarding the device 10. The device 100 is at least partially linearized (i.e., the coil shape is at least partially uncoiled into a generally linear shape) for delivery via a delivery catheter and deployed.

The device 100 is especially useful for closing lumens that have large diameters relative to their lengths and lumens in which a treatment device is subjected to forces from multiple directions. Examples of these types of lumens are ASD, PFO, and PDA's. The device 100 is useful in occluding these lumens because the distal end of the frame 102 can be placed on one side of the lumen (i.e. in the atrium or pulmonary artery), the plug 12 positioned substantially within the lumen, and the proximal end on the other side of the lumen. Since the frame 102 tends to revert to its original substantially helical configuration, it tends to exert force on both sides of the septum or ductus, thus sandwiching the plug in the lumen.

Figure 7:
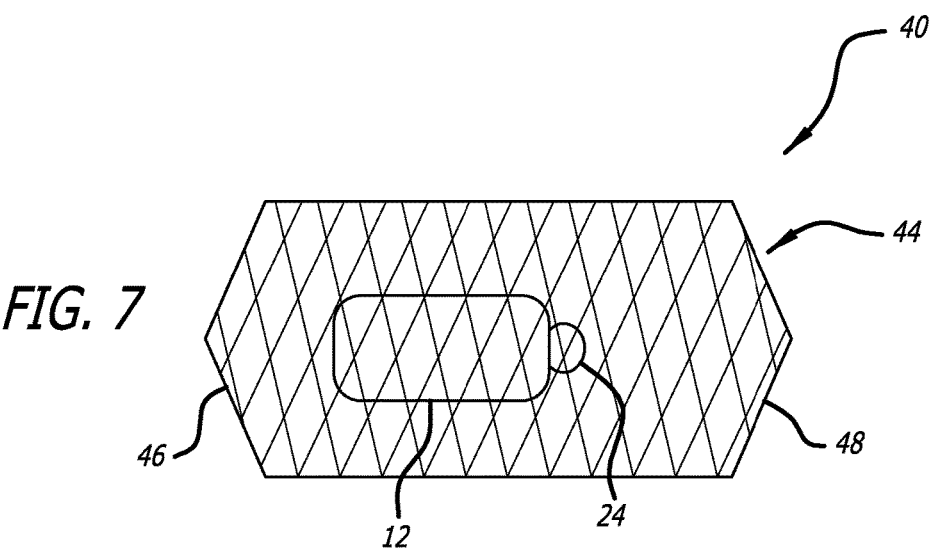
FIG. 7 is a side elevation view of a portion of a device according to one embodiment of the present invention.

In another embodiment of the present invention, as shown in FIG. 7, a device 40 employs a frame 44 that is generally similar to the previously described frame 14, except that a distal end portion 46 and a proximal end portion 48 of the frame 44 are closed such that an interior of the frame is at least partially closed-off. This configuration prevents the plug 12 from migrating in one or both directions in the event that the thread 24 holding the plug 12 in place breaks or if the hydrated plug 12 could not be anchored by the thread 24 alone.

Figure 8:
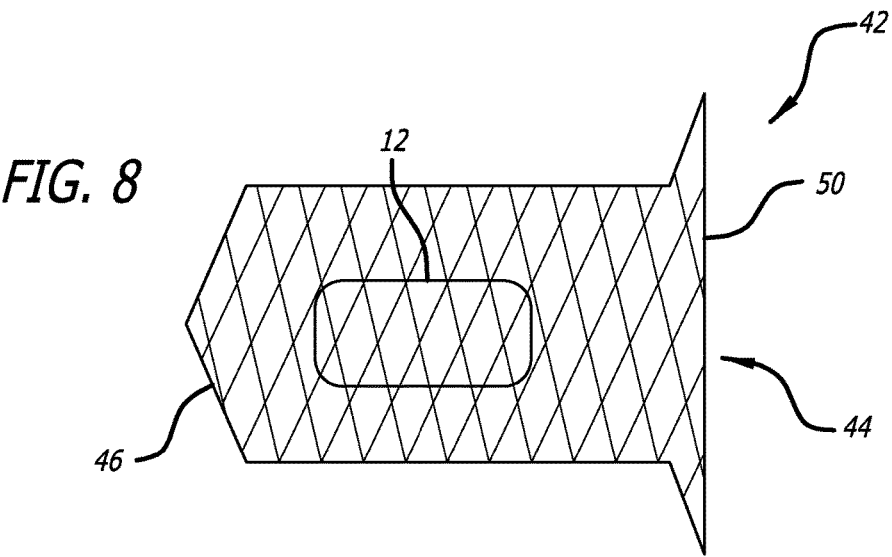
FIG. 8 is a side elevation view of a portion of a device according to one embodiment of the present invention.

In another embodiment, as shown in FIG. 8, the device 42 employs a frame 44 as previously described, except that the upstream, proximal end 50 remains open and preferably at least partially flared. In this configuration, the plug 12 may, but need not be, attached to the frame by a thread 24. As the downstream or distal end 46 of the frame 44 is closed, the plug 12 is prevented from migrating downstream. In such a configuration, the plug 12 may be delivered into the frame as a separate step during deployment of the device.

In yet another embodiment, one or both ends of the frame are at least partially closed or covered with, for example, a mesh, crossing or interwoven threads, or fabric. This covering can be attached over either open or closed ends of the frame and prevents the plug 12 from migrating away from the frame and target.

Figure 9:
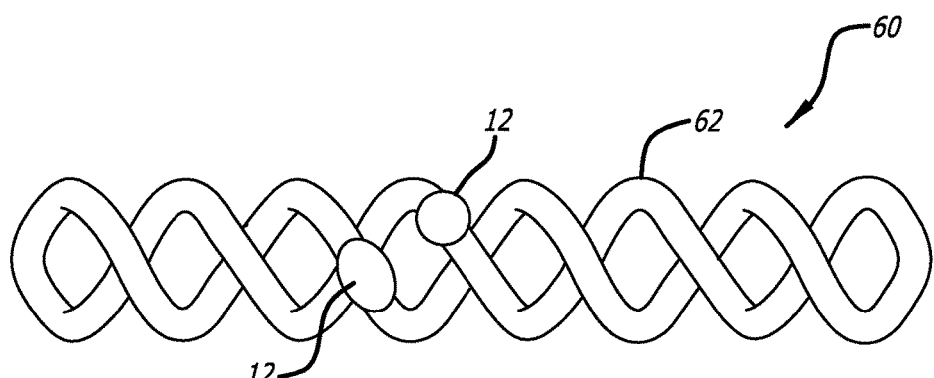
FIG. 9 is a side elevation view of a device according to one embodiment of the present invention.

In one embodiment, as shown in FIG. 9, a device 60 includes a frame 62 comprising a twisted wire that forms a corkscrew shape. Generally, the twisted wire of the frame 62 can form uniform-sized loops so as to maintain a relatively uniform or linear shape. However, the loops of the frame 62 may also have varying sizes so as to form a triangular, conical, or hourglass shape. The plug 12 is attached to the frame 62 directly by skewering the wire or coil through one or more plugs 12 or by using the thread 24 or wire to tether the plug(s) 12 to the frame. Preferably, the frame 62 is sized to have a diameter or height that will be approximately the same size or somewhat larger than the target lumen. The device 60 can be loaded into a delivery catheter by compressing it into a linear configuration (e.g., by physically decreasing the size of the loops) within a lumen of the catheter or onto a delivery pusher. As the device 60 is pushed or released into the target lumen, it expands to its relaxed, twisted configuration.

Figure 10A:
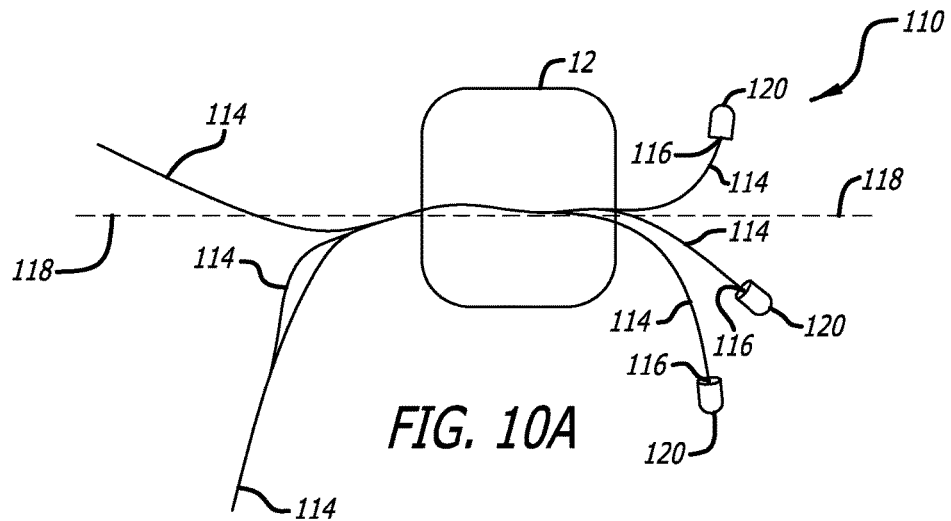
FIG. 10A is a side elevation view of a device according to one embodiment of the present invention.
Figure 10B:
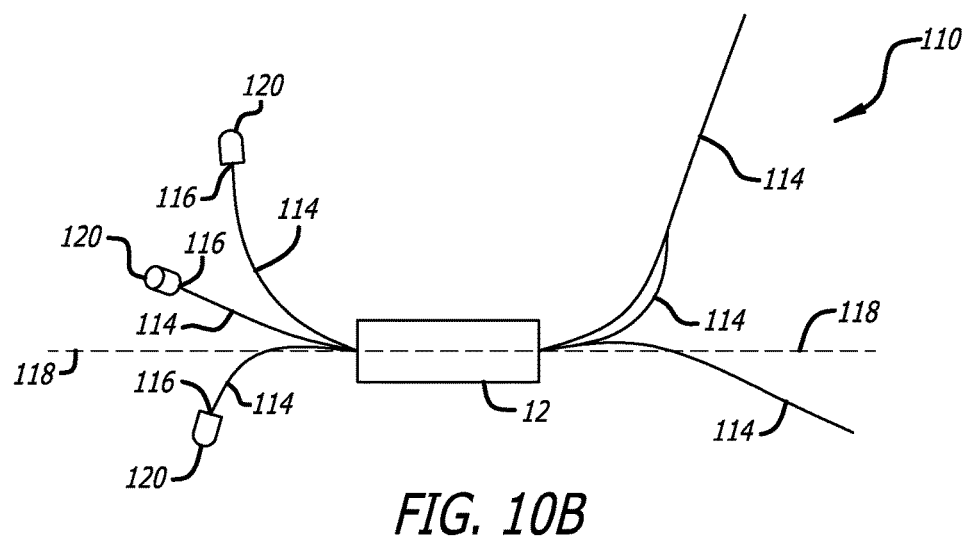
FIG. 10B is a side elevation view of a device according to one embodiment of the present invention.

FIGS. 10A and 10B illustrate yet another embodiment of an occlusion device 110 that comprises a plug 12 through which a plurality of filaments or wires 114 pass through. The plug 12 is formed of, for example, hydrogel or other similar expansile material such as PVA or foam. The wires 114 are passed through the plug 12 along an approximate central axis 118 of the device 110. The wires 114 are configured (e.g., pre-shaped) to curve or bend away from each other in a radial direction relative to the central axis 118. In one example, the wires 114 bend or extend away from the approximate central axis 118 for a length of approximately 6 millimeters.

The wires 114 can be radially oriented in a uniform spacing, such as approximately 120 degrees apart, or in any variety of symmetrical and asymmetrical, non-uniform spacing, such as 100, 130, 130 degrees. In one example configuration, the wires 114 are composed of a shape memory material such as Nitinol, have a diameter of about 0.003 inches, and have ends that are capped with radiopaque markers 120. Alternatively, the wires 114 may be formed by laser cutting a hypotube to the desired dimensions of the wire 114.

The device 110 is particularly useful for closing a PDA. The device 110 can be collapsed into a delivery system and delivered to a target site by conventional means. In one example, the plug 12 expands to a dimension of about 0.185 inches after deployment and closes off or otherwise seals the target site (e.g., a PDA). The expanded and radially curved wires 114 are preferably deployed on either side of the defect and thereby provide support for the plug 12 so as to prevent migration. It should be noted that the device 110 may include any number of wires 114, but preferably between at least 2 and 20 wires, and more preferably at least 3-6 wires. Advantageously, the device 110 is relatively simple to construct and tends to have a smaller delivery profile as compared with many other device shapes.

While the previously described embodiments have included the use of an expandable plug 12, it is also possible to use one or more of these devices without a plug 12. More specifically, a material can be added upstream or adjacent to the deployed device so as to cause the blockage. For example, one or more embolic coils (which may or may not include an expandable material such as hydrogel), can be delivered within the deployed and expanded device.

Figure 11:
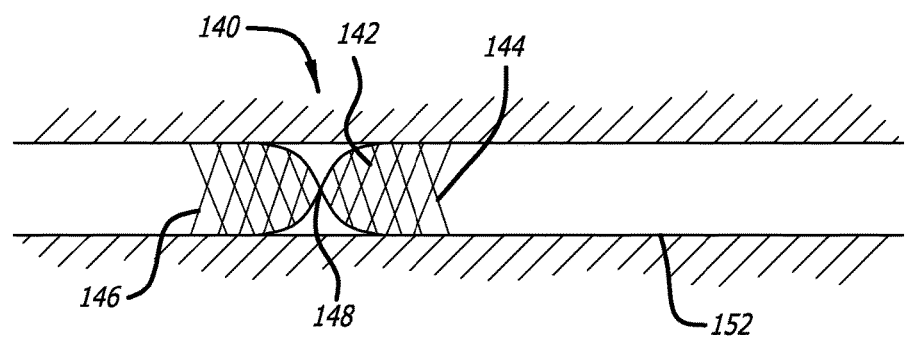
FIG. 11 is a side elevation view of a device according to one embodiment of the present invention.
Figure 12:
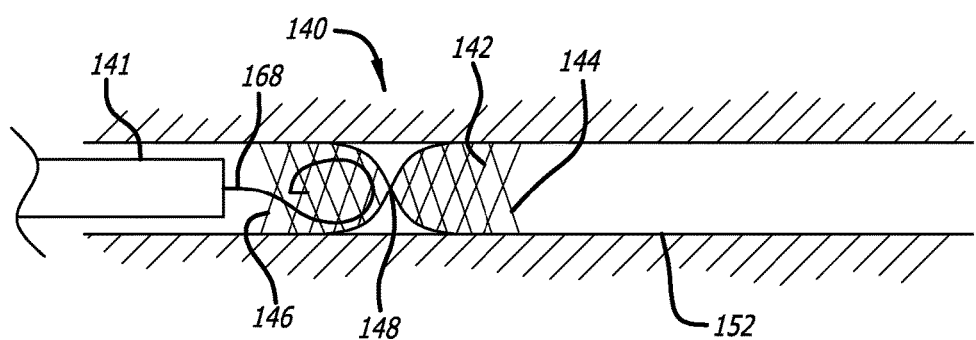
FIG. 12 is a side elevation view of the device seen in FIG. 11.

FIGS. 11 and 12 illustrate one such example of an intravascular self-expanding stent-type device 140 that can be filled with embolic materials such as embolic coils 168. Other embolic material, such as a liquid embolic material (e.g. Onyx), embolizing beads (e.g. Embosphere), or other embolizing agents can also be used. The device 140 comprises a frame or a support structure 142 that is circumferentially open on both a distal end 144 and a proximal end 146, as described above regarding frame 14. A cinched center section 148 creates an embolic material capture region that obstructs the central lumen of the device 140, thereby acting as a stable barrier for subsequent embolic material delivery. The center 148 can be woven together or fastened by a thread, wire, clip or other fastening member and allows for a decreased diameter and controlled deployment.

Once the device 142 is deployed at a target occlusion location, a second delivery catheter 141 (or possibly the same delivery catheter) is advanced to the proximal end 146 of the device 142 and embolic material is deployed into the proximal half of the device 142. In this example, the embolic material is one or more embolic coils 168. These embolic coils 168 may include an expansile coating (such as hydrogel) that expands within a patient's blood or may include expansile material that is separate from the coils 168. In this respect, half of the device 142 is filled with material, thereby occluding most of the blood flow through the lumen 152. Over time, this occlusion will likely become completely blocked by expansion of any expansile coating on the embolic coils 168, clotting of the blood and/or tissue growth over the embolic coils 168.

Figure 13:
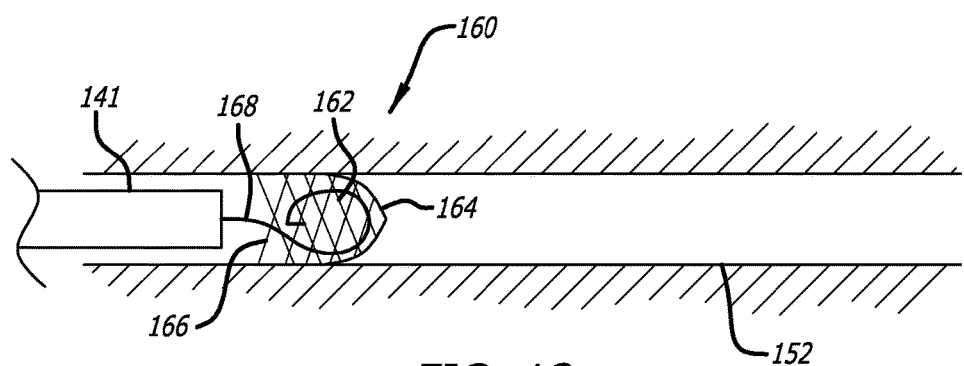
FIG. 13 is a side elevation view of a device according to one embodiment of the present invention; and, FIG. 14 is a side elevation view of a device according to one embodiment of the present invention.

FIG. 13 illustrates an intravascular self-expanding stent-type device 160 that is generally similar to the previously described device 42 of FIG. 8, but without the plug 12. The device 160 comprises a frame 162 that facilitates lumen occlusion when used in conjunction with an embolic coil 168 or other embolic materials. Only a downstream or distal end 164 of the frame 162 is at least partially closed and a proximal end 166 is open, as described above regarding the frame 14.

As with the previous embodiment, the device 162 is delivered to a desired occlusion point in a lumen 152. Next, the distal end of the delivery catheter 141 is positioned adjacent or even partially inside of the framework 162 and the embolic coils 168 are deployed within the device 160. Since the downstream or distal end 164 of the frame 162 is closed to act as a stable barrier, the embolic coil 168 is prevented from migrating downstream through the lumen 152, thus occluding the lumen 152. Again, other embolic materials, such as hydrogel, may be used in conjunction with device 160 and embolic coils 168.

Alternately, both ends of the device 162 may be closed and the embolic material, such as embolic coils 168 can be delivered inside a cavity of the device, through apertures in the weaving. For example, an embolic coil deliver catheter can be inserted through an aperture created by its woven wires and the embolic coil can be advance into the device 162.

Figure 14:
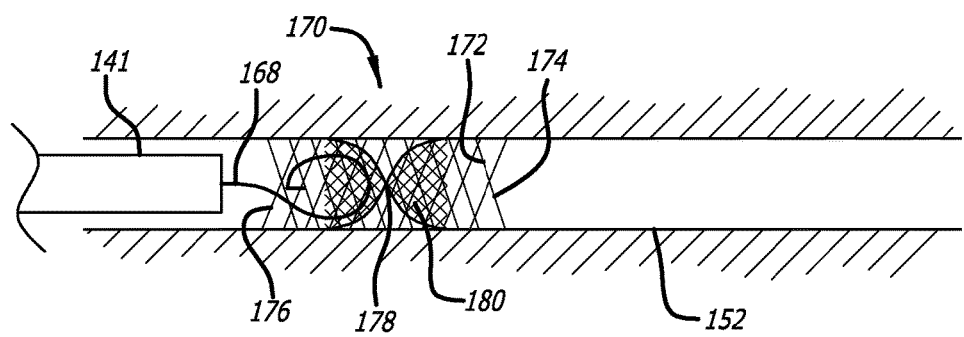

FIG. 14 illustrates a dual-layer stent device 170 that includes an outer, anchoring stent layer 172 and an inner, occluding stent layer 180. Generally, this dual-layer stent device 170 is similar to and can be constructed according to the teachings in U.S. application Ser. No. 13/003,277 filed Jan. 7, 2011 and U.S. application Ser. No. 13/311,430 filed Dec. 5, 2011, the contents of which are incorporated herein by reference. The outer stent layer 172 expands against the lumen 152 to anchor the device 170 against the lumen 152 while the inner stent layer 180 is cinched near a middle location 178 to form an hourglass shape. Alternately, the inner stent layer 180 can be cinched at its distal end to create a shape similar to that of device 160 in FIG. 13.

Preferably, occluding material, such as embolic coils 168 can be delivered into the proximal end 176 of the device 170 to occlude the lumen 152. The inner stent layer 180 may be coated in an expansile material, such as hydrogel, in addition to or in place of the discretely-added occluding material.

The outer, anchoring stent layer 172 is preferably composed of one or more wires having a larger diameter than those composing the inner, occluding stent layer 180. Additionally, the outer layer 172 can be woven to have apertures that are larger than those of the inner stent layer 180, when both layers are in an expanded configuration. In this respect, the outer layer 172 can provide relatively more radially outward force for anchoring while the inner layer 180 can provide a relatively finer-woven occlusive barrier.

Preferably, the inner stent layer 180 is connected to the outer stent layer 172 at its proximal end and optionally at its distal end. Additionally, the inner stent layer 180 can be located near the outer stent layer's proximal end 176, distal end 174, middle, or any positions therebetween.

The device 170 has several advantages compared to prior art lumen obstruction devices that occlude a lumen by preventing dislodgement of embolization coils, The present invention allows partial deployment of re-sheathing due to its attachment mechanism, allowing for a more controlled placement of the device. Further, the present invention can be used with much smaller catheters, conceivably down to 1.7 French compared to a 5 French or greater sized catheter. This allows the present invention to navigate more tortuous and distal lumens, thereby being able to treat a wider range of patients. Additionally, this allows the same catheter to be used to deliver both the device and the embolic coils and materials. Further, the present invention minimizes any trauma imposed on the lumen wall by using a self-expanding radial force tuned for the artery size.

The previously described device, such as 140, 160, and 170, can be made with a variety of materials including, but not limited to bioactive, thrombogenic, hydrogel, or other therapeutic coatings. Further, these devices can be made in a variety of different sizes and lengths and can be cinched or enclosed at any location along the length of the stent. To improve clinical outcomes, the device can be coated with, for example, bioactive or hydrogel coatings. The device can be used with varying porosities to provide full or partial flow occlusion to limit the amount of embolic materials required to sufficiently occlude a lumen.

Delivery of the above described devices can be accomplished using various delivery systems. For example, the device can be delivered by pushing the device through a catheter or sheath with a specialized pusher or a guidewire by attaching one or both ends of the device to a delivery pusher that holds the device so that it can be positioned and repositioned within the lumen. The device is then selectively detached from the delivery system by, for example, mechanically, thermally, hydraulically, or electrolytically severing an attachment member associating the device and the delivery system.

In one embodiment, the device incorporates at least one radiopaque marker band positioned at one end of the device. The marker is configured to interlock to a mating element on a delivery pusher. The user can partially deploy and retrieve the device using the interlock to pull back on the device. Release of the device from the delivery system is, for example, accomplished by pushing most of the implant out of the delivery catheter and/or retracting the delivery catheter to expose the interlock release(s).

In another embodiment, a monofilament is wrapped through the proximal end of the device and then attached to a delivery pusher incorporating a heater that can be activated by electrical current. The user can fully or partially deploy the device and then reposition or recover the device if needed. When the device is in the desired location, the user activates the heater thereby causing the monofilament to break from and release the device.

In yet another embodiment, one end of the device incorporates an atraumatic tip while the other end is soldered to a delivery pusher. The user can deploy and reposition the device as needed, and then pass a current through the delivery pusher. The current causes the solder to corrode at an accelerated rate in the patient's blood and to release the end of the device that was soldered to the pusher.

Alternatively, the end of the device incorporates a coupling element such as a tube of radiopaque material that is configured to allow a heat-severable thread having two ends to pass through the coupling. One end of the thread is tied to the device and the other end of the thread is passed through a heater incorporated into the end of a delivery pusher. The device is detached by the user as previously described.

In another embodiment, the delivery system includes a sheath disposed over a pusher member. A stent device is compressed over a distal end of the pusher and the sheath is placed over the stent. In this respect, the stent is maintained in place, in part, via frictional forces. Additional details of such a delivery system can be found in U.S. application Ser. No. 13/003,277 filed Jan. 7, 2011 and U.S. application Ser. No. 13/311,430 filed Dec. 5, 2011, both of which were previously incorporated by reference in this specification.

The present device and method has several advantages over the prior art. In comparison to prior art detachable balloons, the device of the present invention is easier to place, requires fewer steps to deploy, and has a lower tendency to migrate after placement if, for example, a balloon-based device starts to leak over time.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An occlusion device comprising:
   a stent comprising a woven tubular support structure having a compressed configuration and an expanded configuration, wherein said woven tubular support structure is configured to self-expand to said expanded configuration, forming a plurality of radially projecting loops on a proximal and distal end of said stent and forming an elongated passage therethrough terminating with a proximal opening and a distal opening;
   a plug comprising hydrogel and having a compressed dehydrated state and an expanded hydrated state and self-expanding from a compressed configuration due to the presence of liquid to an expanded configuration the plug fixed within said tubular support structure, said plug compressed from an initial size prior to insertion within said stent and thus being of substantially smaller diameter than said woven tubular support structure when said tubular support structure is in said expanded configuration, said plug further utilizing a powdered visualization agent; and,
   a thread having a first end and a second end, and being skewered through substantially an entire length of said plug and around a wire of said woven tubular structure; said first end being fixed to said second end to form a loop and so as to fix said plug to said woven tubular structure in both said compressed dehydrated state and in said expanded hydrated state and so as to maintain said thread from extending beyond said proximal opening and said distal opening.

2. An occlusion device comprising:
   a stent comprising a woven tubular frame structure forming a passage therethrough; said tubular frame structure having a compressed configuration and an expanded configuration, and a plurality of radially projecting loops at a proximal and distal end of said stent; and
   a plug solely comprising expansile material in the form of hydrogel, having a compressed dehydrated state and an expanded, hydrated state; the presence of a liquid causing said plug to expand, said plug compressed from an initial size prior to insertion within said stent and thus being of substantially smaller diameter than said woven tubular support structure when said tubular support structure is in said expanded configuration, said plug further utilizing a powdered visualization agent; and,
   a thread having a first end and a second end passing around a wire forming said woven tubular frame structure and fixing said plug within said passage in said compressed dehydrated state and in said expanded hydrated state; said thread being skewered through substantially an entire length of said plug and said first end being fixed to said second end to form a loop and said thread only extending along a portion of said woven tubular frame structure.

3. The occlusion device of claim 2, wherein said tubular frame structure is formed from a single wire.

* * * * *